(12) United States Patent
Kim

(10) Patent No.: US 6,270,524 B1
(45) Date of Patent: Aug. 7, 2001

(54) FLEXIBLE, RADIALLY EXPANSIBLE LUMINAL PROSTHESES

(75) Inventor: Steven W. Kim, Sunnyvale, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/134,494

(22) Filed: Aug. 14, 1998

Related U.S. Application Data

(62) Division of application No. 08/747,920, filed on Nov. 12, 1996, now abandoned.

(51) Int. Cl.$^7$ .............................. A61F 2/06; A61M 29/00
(52) U.S. Cl. ................. 623/1.15; 623/1.11; 606/194
(58) Field of Search ..................... 623/1.1, 1.13, 623/1.15, 1.16, 1.35, 1.12, 1.17

(56) References Cited

U.S. PATENT DOCUMENTS

| | | | |
|---|---|---|---|
| 5,102,417 | 4/1992 | Palmaz | 606/195 |
| 5,104,404 | 4/1992 | Wolff | 623/1 |
| 5,135,536 | 8/1992 | Hillstead | 606/195 |
| 5,195,984 | 3/1993 | Schatz | 606/195 |
| 5,275,622 | 1/1994 | Lazarus et al. | 623/1 |
| 5,282,824 | 2/1994 | Gianturco | 606/195 |
| 5,375,612 | 12/1994 | Cottenceau et al. | 128/899 |
| 5,383,892 | 1/1995 | Cardon et al. | 606/198 |
| 5,397,355 | 3/1995 | Marin et al. | 623/12 |
| 5,421,955 | 6/1995 | Lau et al. | 216/48 |
| 5,443,496 | 8/1995 | Schwartz et al. | 623/1 |
| 5,449,373 | 9/1995 | Pinchasik et al. | 606/198 |
| 5,545,210 | 8/1996 | Hess et al. | 623/1 |
| 5,591,197 | 1/1997 | Orth et al. | 606/198 |
| 5,674,278 | 10/1997 | Boneau | 623/1 |
| 5,755,781 | * 5/1998 | Jayaraman | 623/1.15 |
| 5,776,161 | * 7/1998 | Globerman | 606/194 |
| 5,824,040 | * 10/1998 | Cox et al. | 623/1.35 |

FOREIGN PATENT DOCUMENTS

| | | | |
|---|---|---|---|
| 0 364 787 A2 | 4/1990 | (EP) | A61F/2/06 |
| 540 290 A2 | 5/1993 | (EP) | A61F/2/06 |
| 606 379 | 12/1995 | (EP) | A61F/2/06 |
| WO 92/06734 | 4/1992 | (WO) | A61M/29/00 |
| WO 95/31945 | 11/1995 | (WO) | A61F/2/06 |
| WO 96/26689 | 9/1996 | (WO) | A61F/2/06 |

* cited by examiner

*Primary Examiner*—David H. Willse
*Assistant Examiner*—Alvin Stewart
(74) *Attorney, Agent, or Firm*—Sterne, Kessler, Goldstein & Fox P.L.L.C.

(57) ABSTRACT

The present invention provides methods and apparatus for deploying luminal prostheses, such as stents, grafts, or stent-grafts, to luminal walls at a target site within an anatomical lumen. In one aspect of the invention, luminal prostheses are designed to negotiate curves, bends and other irregularities in body passageways so as to facilitate deployment of the stents and to minimize injury to the luminal walls. In addition, the luminal prostheses of the present invention have sufficient flexibility to bend and articulate so as to substantially conform to a tortuous body lumen at the target site, which enhances the post-deployment performance of the stent. In another aspect of the invention, methods and apparatus are provided for securing luminal prostheses to the luminal walls at a target site within an anatomical lumen. These methods and apparatus provide an effective frictional lock between the stent and the luminal wall to inhibit migration and/or failure of the stent.

30 Claims, 15 Drawing Sheets

FLEXIBLE, RADIALLY EXPANSIBLE LUMINAL PROSTHESES

This application is a division of and claims the benefit of U.S. application Ser. No. 08/747,920, filed Nov. 12, 1996, now abandoned. The disclosure of which is herein incorporated by reference.

BACKGROUND OF THE INVENTION

1. Field of the Invention

The present invention relates generally to radially expansible intraluminal prostheses, such as grafts, stents, stent-grafts and the like. More particularly, the invention provides a flexible stent structure for delivery through irregular or curved body lumens in the vasculature, and for deployment at a target site in a tortuous body lumen. The stent structure may also have a plurality of axially extending anchor members for securing the stent structure to the luminal wall at the target site.

Luminal prostheses, commonly known as grafts, stents or stent-grafts, are tubular-shaped devices which function to hold open a segment of a blood vessel or other anatomical lumen. These stent-grafts, stents and grafts are provided for a variety of medical purposes. For example, stents can be placed in various body lumens, such as blood vessels and the ureter, urethra, biliary tract and gastrointestinal tract, for maintaining patency. Stents are particularly suitable for supporting dissections in the arterial tissue that may occur during, for example, balloon angioplasty procedures. Such dissections can occlude an artery and prevent the flood of blood therethrough. In addition, stents may be used to support grafts to form a stent-graft for lining or replacing weakened blood vessels, such as in aortic aneurysm repair procedures (e.g., aneurysms occurring in the abdominal aorta, usually beginning below the renal arteries and often extending distally into one or both of the iliac arteries).

An important consideration in deploying stents in the vasculature is the ability of the stent to anchor into the vessel to hold open the vessel and to prevent migration of the stent due to loads applied to the stent. Once deployed, the stent may be subjected to a variety of loads, such as blood flowing through the stent or the expansion and contraction of the blood vessel from the patient's heart beat. One of the mechanisms for anchoring a stent to a vessel is the outward radial force applied by the stent against the luminal wall after the stent has expanded to its final enlarged diameter within the body lumen. Unfortunately, it is often difficult to accurately predict the degree of radial force that will be exerted by an individual stent once it has been deployed and expanded within the patient's vasculature. A relatively low radial force exerted against the luminal wall may allow the stent to migrate along the body lumen and/or fail to adequately maintain lumen patency. This could cause potential injury to the patient and often requires another surgical procedure to remove the failed stent and deploy a second stent at the same portion of the diseased vessel or to effect surgical repair of the vessel. On the other hand, a relatively high radial force may potentially damage the luminal wall, e.g., by causing abnormal vessel distention or contributing to aneurysmal growth.

Another important consideration in deploying and implanting stents is the ability of the stent to pass through curvatures, bend and other irregularities within the body passageways during deployment, and to conform a tortuous body lumen at the target site after the stent has been implanted. Many stents and stent-grafts, particularly those which are relatively rigid, do not have the requisite ability to bend so as to conform to the curves and bends present within the vasculature. To overcome this deficiency, recent stents have been manufactured from a plurality of rigid tubular rings that are connected to each other with flexible connecting structures, such as hinges, springs or the like. The flexible connecting structures allow adjoining rigid rings to pivot relative to each other so that the entire stent may flex along its length within the delivery catheter. Although these recent stents have some ability to conform to and to negotiate curves and bends, they still present deployment problems. For example, the rigid tubular rings may become stuck or jammed as the connecting structures bend around curves in the body passageway. Often, the surgeon must apply force to the delivery catheter to urge the catheter and the stent around the curve and continue its progress through the body passageway. This hinders the deployment process, and may injure the luminal wall. In addition, these rigid tubular rings generally do not conform well to a tortuous body lumen at the target site, which can cause performance problems after the stent has been deployed.

For these and other reasons, it would be desirable to provide methods and apparatus for securely anchoring stents, grafts or stent-grafts to luminal walls after the stent has expanded within the body lumen to decrease migration and/or failure of the stent. It would be further desirable to provide stents with a geometry and sufficient flexibility such that the stents conform to curves and bends in the patient's vasculature to facilitate deployment of the stent at the target site, and to enhance the performance of the stent after it has been implanted.

2. Description of the Background Art

U.S. Pat. Nos. 5,104,404 to Wolff, 5,443,496 to Schwartz and 5,195,984 to Schatz each describe an articulated stent having a number of rigid stent segments connected together with flexible hinges, such as wire, or coiled wire. The stent segments each generally comprise a plurality of V-shaped elements connected together. U.S. Pat. No. 5,449,373 to Pinchasik describes an articulated stent with a plurality of substantially rigid segments coupled together with flexible connectors having one or more kinks for advancing through curved body lumens. U.S. Pat. No. 5,282,824 to Gianturco describes a self-expanding stent having a plurality of Z-stents connected together and covered by a flexible nylon sleeve. European Patent Application 540 290 A2 to Advanced Cardiovascular Systems, Inc. discloses an expandable stent made up of a plurality of radially expandable cylindrical elements interconnected by axial elements. The stent is formed by removing exposed portions of a tubing by an etching process. U.S. Pat. No. 5,102,417 to Palmaz illustrates an expandable vascular graft having thin-walled tubular members with a plurality of longitudinal slots. The tubular members are connected together with flexible spiral connectors.

SUMMARY OF THE INVENTION

The present invention provides methods and apparatus for deploying luminal prostheses, such as stents, grafts, or stent-grafts, to luminal walls at a target site within an anatomical lumen. In one aspect of the invention, luminal prostheses are designed to negotiate curves, bends and other irregularities in body passageways so as to facilitate deployment of the stents and to minimize injury to the luminal walls. In addition, the luminal prostheses of the present invention have sufficient flexibility to bend and articulate so as to substantially conform to a tortuous body lumen at the target site, which enhances the post-deployment performance of the stent. In another aspect of the invention, methods and apparatus are provided for securing luminal prostheses to the luminal walls at a target site within an anatomical lumen. These methods and apparatus provide an effective mechanical lock between the stent and the luminal wall to inhibit migration and/or failure of the stent.

In a first aspect, the apparatus of the present invention is a radially expansible luminal prosthesis including a plurality of open ended tubular stent frames spaced along the longitudinal axis of the prosthesis and connected together with one or more connecting structures. Preferably, the connecting structures are rigid links that extend between adjoining stent frames for movably connecting the frames to each other, thereby allowing flexing of the prosthesis along its longitudinal axis. The connecting structures are sufficiently rigid to maintain a substantially constant distance between adjoining stent frames at the connection points. The tubular stent frames, on the other hand, are sufficiently flexible so that at least portions of each stent frame will deform as the stent passes around, or is positioned in, curves or bends in a body passageway. In the preferred configuration, the stent frames will deform as much as necessary (or possible) to conform to the inner luminal wall with this deformation being limited by the rigid connecting structures. Thus, the stent frames may deform in three dimensions (i.e., radially and/or axially) depending on the amount of curvature of the body lumen and the angle of the fixed connecting structures.

In a specific configuration, the connecting structures are substantially rigid links, such as wires, tubes, or the like, that define a constant length between adjoining stent frames along the rigid links. The rigid connecting structures provide column stiffness to the stent, and they allow the flexible stent frames to deform and move relative to each other, which provides greater flexibility to the stent. Preferably, three rigid links are spaced uniformly around the circumference of the stent frames to form a tripod design that provides sufficient structure and axial strength to the stent. During deployment, the interstitial spaces between the three rigid links allow the stent to bend sufficiently to negotiate the tortuous lumens in the vasculature. After the stent has been implanted at the target site, these interstitial spaces allow portions of the adjoining stent frames to deform axially and radially so as to conform to the geometry of the body lumen. Preferably, each group or tripod of rigid links are staggered relative to adjacent link groups along the longitudinal axis of the stent to provide additional flexibility to the stent. In addition, this arrangement allows the stent to conform to curves and bends in body passages regardless of the orientation of the rigid links relative to the curves in the body passages.

The stent frames each comprise a plurality of body segments connected together to form each stent frame. The body segments may comprise a variety of shapes, such as U, V, Z, N, diamond or other shapes. In a preferred embodiment, the stent frames are each formed by a plurality of V-shaped segments connected together at their ends to form a plurality of intersection points extending circumferentially around each stent frame. In an alternative embodiment, the stent frames are each formed by a plurality of diamond shaped segments that include a pair of laterally facing points and a pair of axially facing points. The diamond shaped segments are preferably connected together at the laterally facing points to form the tubular frame.

In another aspect of the invention, methods and apparatus are provided for securing luminal prostheses to luminal walls at a target site within an anatomical lumen. These methods and apparatus provide an effective mechanical lock between the stent and the luminal wall to inhibit migration and/or failure of the stent. This mechanical lock is provided by creating an additional mechanical lock between the stent and the inner surface of the luminal wall, rather than increasing the radial force applied by the stent, which minimizes injury to the vessel wall that may be caused by large radial forces, such as aneurysmal growth, abnormal vessel distension and the like.

In this aspect, the apparatus of the present invention is a radially expansible luminal prosthesis that generally includes one or more tubular stent frames with open ends. Each stent frame includes a plurality of anchor members or protrusions that extend axially from the associated segments. The anchor members provide an additional mechanical lock between the stent frame and the luminal wall to help secure the luminal prosthesis at the target site. Stents are typically subject to a variety of loads including fluids, such as blood, flowing through the vessel, expansion and contraction of the blood vessel during the continuous pulse of the patient and the like. The anchor members will usually provide sufficient friction/anchoring between the luminal wall and the stent to prevent migration of the prosthesis from the target site due to the loads applied after the prosthesis has been deployed. The anchor members may have rounded, traumatic ends to minimize injury to the luminal wall, or they may have ends that taper to a sharp point to penetrate the luminal tissue when these loads reach a high enough level to overcome the friction forces, thereby preventing migration of the stent.

Another advantage of the present invention is that the anchor members physically lock the stent to the luminal wall, which helps to decrease stent failure. Stent failure can include the loss of sufficient hoop strength to maintain lumen patency or hold the prosthesis in place within the lumen, and other breakdowns in the tubular body that result in the inability of the stent to perform a desired function within a body lumen. Decreasing failure of the stent increases the lifetime of the stent, which minimizes second and third operations that may be necessary or desirable to remove and replace a stent that has completely failed or migrated to a different location within the vasculature. In addition, increasing the stent's lifetime will minimize exposure of the patient to the consequences of failed or migrated stents, such as fluid leakage, aneurysm rupture, etc.

In a specific configuration, the luminal prosthesis includes at least two tubular stent frames coupled together by a connecting structure, such as a mechanical link, a hinge, a spring, or the like. In a particularly preferred embodiment, the connecting structure is a rigid link that maintains a substantially constant distance between adjoining stent frames (as discussed in the previous embodiment). Alternatively, the stent frames may be attached to a graft liner, such as a polymeric sheet, that is suitably bonded to the stent frames. The graft liner may cover the entire stent, or selected portions of the stent to, for example, inhibit cell proliferation while maintaining the stent flexibility. The stent frames are preferably spaced from each other by the connecting structure so as to define annular interstitial spaces therebetween. As the luminal prosthesis expands radially outward against an anatomical lumen, portions of the luminal wall are forced into the interstitial spaces between the stent frames. If loads within the lumen reach a threshold level to move the prosthesis, the anchor members dig into the luminal wall portions to effectively form a substantially continuous, interlocking mechanical wall with these luminal wall portions and the stent frames.

In one embodiment, the stent frames are each formed by a plurality of V-shaped segments connected together at their ends to form a plurality of intersection points extending circumferentially around each stent frame. One or more anchor members extend axially from a group of these intersection points into the interstitial spaces between adjoining stent frames. Usually, the V-shaped elements in adjoining stent frames are staggered relative to each other to minimize contact between opposing anchor members and to help distribute the anchor members uniformly around each interstitial space. The anchor members preferably end at sharp points designed to pierce tissue from the luminal wall and secure the stent thereto.

In another embodiment, the stent frames are each formed by a plurality of diamond shaped segments that include a pair of laterally facing points and a pair of axially facing points. The diamond shaped segments are preferably connected together at the laterally facing points to form the tubular frame. One or more anchor members extend axially from the axially facing points of a group of the diamond-shaped segments.

In a method according to the present invention, a stent, graft or stent-graft is provided with a plurality of flexible tubular frames connected by rigid links and having anchor members extending axially into spaces between adjoining frames. The stent is compressed into a narrow-diameter configuration, and advanced endoluminally to the target site with a delivery catheter. Typically, the delivery catheter and the stent will pass through one or more small curves, bends or other irregularities in the body passageways as it is being delivered to the target site within the catheter. As the stent is directed around each curve, adjoining flexible stent frames deform enough to substantially conform to the inner luminal wall. For example, the portions of the stent frames on the outer side of the curve will generally move away from each other, while the portions of the stent frames on the inner side move towards each other and deform inward to approximate the shape of the inner side of the curve. This facilitates deployment of the stent and minimizes injury to the luminal wall.

Once the stent has been positioned at the target site, the tubular stent frames are then radially expanded against the luminal wall by suitable mechanisms, such as expansible balloons, other mechanical expanders, shape memory alloy material or the like. The flexible characteristics of the stent also improve its performance after deployment. For example, the stent will substantially conform to the curves and irregularities of a tortuous lumen, which reduces the stresses or loads placed against the stent. In addition, this flexibility increases the stent's ability to perform its intended function within the lumen, e.g., maintain lumen patency, inhibit occlusive growth and the like.

The radial expansion of the stent frames during stent deployment forces portions of the luminal wall into the interstitial spaces between adjoining stent frames, thereby increasing the friction between the luminal wall and the stent frames. If the loads acting against the stent overcome this friction and begin to move the stent relative to the luminal wall, the axially extending protrusions of the stent frames penetrate these tissue portions to secure the stent structure to the luminal wall. This decreases migration of the stent or other stent failure, while minimizing injury to the luminal wall.

DESCRIPTION OF THE PREFERRED EMBODIMENT

Figure 1:
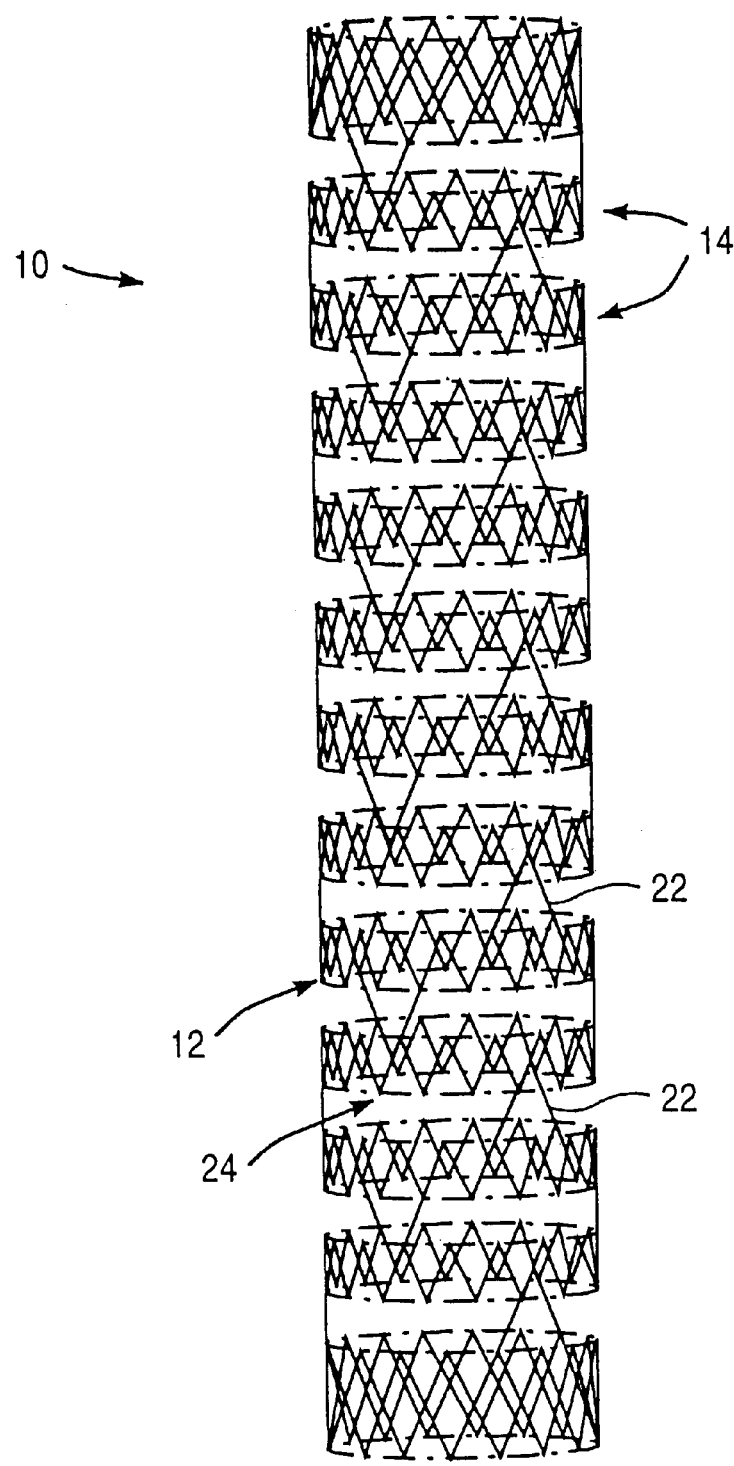
FIG. 1 illustrates an exemplary stent structure having a plurality of stent frames in an expanded configuration according to the present invention.

The present invention provides methods and apparatus for securing radially expansible intraluminal tubular prostheses, particularly grafts, stents or stent-grafts, to a target site within an anatomical lumen. The present invention will be extremely useful with stents or stent-grafts suitable for minimally invasive placement within the vasculature for the treatment of diseases, such as aneurysms, stenoses, and the like. The stents will be capable of being compressed into a narrow-diameter configuration to facilitate introduction into the body lumen, typically during surgical cutdown or percutaneous introduction procedures. Once deployed at a target site within a body lumen by a suitable delivery catheter, the stents will be capable of radially expanding into an enlarged configuration to maintain lumen patency and/or mechanically augment the luminal wall strength. Exemplary delivery catheters and methods for placement of the stents of the present invention are more fully described in co-pending U.S. patent application Ser. No. 08/475,200 (Attorney Docket No. 16380-11-3), the complete disclosure of which is incorporated herein by reference.

The stents or stent-grafts of the present invention each include one or more hollow radially expansible stent frames sized for delivery through an anatomical lumen and having first and second open ends and an inner lumen therebetween. The stent frames each have sufficient flexibility to individually deform radially and/or axially so as to conform to the curvature of an inner luminal wall. In the preferred configuration, the stent frames will deform as much as necessary (or possible) to conform to the inner luminal wall with this deformation being limited by the rigid connecting structures. Thus, the flexible stent frames may deform in three-dimensions (axially and radially (i.e., laterally and vertically)) depending on the amount of curvature of the body lumen and the angle of the fixed connecting structures. In an exemplary embodiment, the stent frames will define a circular cross-sectional shape that may be deformed into a substantially elliptical cross-section as the stent frames conform to a tortuous body lumen. However, stent frames may have shapes other than circular in the nondeformed configuration, such as rectangular, oval, elliptical or the like.

The flexible stent frames are connected together with one or more substantially rigid connecting elements, such as a wire, link, tube or the like. The connecting elements will be sufficiently rigid (compared to the tubular stent frames) to force the stent frames to deform as necessary to conform to a tortuous body lumen. Preferably, the connecting elements are rigid wire links that maintain a substantially constant distance between adjoining stent frames, which forces the stent frames to deform so as to conform to curves or irregularities in body lumens. In addition, the rigid links provide additional column stiffness for the prosthesis, which minimizes axial movement of the stent frames relative to each other when the stent is compressed in the axial direction. This column stiffness is particularly advantageous with stentgrafts that employ inner and/or outer fabric liners because it minimizes wrinkling of the fabric.

In an exemplary embodiment, three wire links are uniformly spaced around the circumference of the stent frames to form a tripod design that provides sufficient structure and axial strength to the stent. Of course, the invention may include more or less than three wire links between adjoining stent frames. However, applicant has found that three connectors provides adequate axial stiffness, while allowing the adjoining stent frames to flex in the longitudinal direction to increase the stent's flexibility. The spaces between the three rigid links allow portions of the adjoining stent frames to move axially toward and away from each other to conform to a tortuous body lumen. In addition, when the stent is in the compressed configuration in the delivery catheter, the connectors in the smaller diameter configuration will bend, allowing the stent to negotiate tortuous body lumens during endoluminal delivery to the target site. Preferably, each group or tripod of rigid links are staggered relative to adjacent link groups along the longitudinal axis of the stent to provide flexibility to the stent, and to allow the stent to conform to curves and other irregularities in body lumens regardless of the orientation of the links relative to the curves in the body passages.

The stent frames of the present invention are typically manufactured from a tubular material, such as tubing made out of shape memory alloy having elastic or pseudo-elastic properties, such as Nitinol™, Elgiloy™, or the like. The tubular member is usually significantly smaller in diameter as compared to the final diameter of the stent in the expanded configuration within the body lumen. Slots are cut into the tubes via laser cutting methods, photo etching, or other conventional methods to form the separate stent frames. For example, these methods include coating the external surface of a tube with photoresist material, optically exposing the etch pattern using a laser beam while translating and rotating the part, and then chemically etching the desired slot pattern of the state using conventional techniques. A description of this technique can be found in U.S. Pat. No. 5,421,955 to Lau, the complete disclosure which is incorporated herein by reference. In other methods, laser cutting technology is used in conjunction with computer controlled stages to directly cut a pattern of slots in the wall of the hypodermic tubing to obtain the desired stent geometry. A description of a typical laser cutting method is disclosed in U.S. Pat. No. 5,345,057 to Muller, the complete disclosure of which is incorporated herein by reference.

Alternatively, the stents may be manufactured from a substantially planar sheet of alloy material, which is stamped, laser cut, photoetched, electro-discharge machined (EDM) or the like to form slots or openings therein. The slotted sheet is then deformed into a tubular configuration by locating a tapered mandrel near the center of the planar sheet, and axially translating the planar sheet over the tapered mandrel. The edges of the planar sheet are folded downward as the sheet is moved over the mandrel to form a tubular configuration. A complete description of this process can be found in co-pending, commonly assigned U.S. patent application Ser. No. 08/593,515, filed Jan. 30, 1996, the complete disclosure of which has already been incorporated herein by reference.

In an exemplary configuration, the stent frames are formed from a resilient shape memory alloy material that is capable of being deformed by an applied stress, and then recovering to its original unstressed shape. The alloy material will usually exhibit thermoelastic behavior so that the stents will transform to the original unstressed state upon the application of heat (i.e., an $A_f$ temperature below body temperature). The prostheses may also exhibit stress-induced martensite, in which the martensite state is unstable and the prosthesis transforms back to the original state when a constraint has been moved (i.e., when the stent is released from an introducing catheter within a body lumen).

The material for the shape memory alloy will be selected according to the characteristics desired of the population of prostheses. Preferably, the shape memory alloy will comprise a nickel titanium based alloy (i.e., Nitinol™), which may include additional elements which affect the characteristics of the prosthesis, such as the temperature at which the shape transformation occurs. For example, the alloy may incorporate additional metallic elements, such as copper, cobalt, vanadium, chromium, iron or the like. A more complete description of an exemplary method for manufacturing shape memory alloy stents can be found in U.S. Provisional Patent Application Serial No. 60/020,963, filed Jun. 25, 1996 (Attorney Docket No. 16380-55), the complete disclosure of which is hereby incorporated herein by reference.

Alternatively, the stent frames may comprise malleable materials other than shape memory alloys, such as stainless steel, tantalum, titanium or the like. In this configuration, the stent frames will preferably be expanded at the target site by conventional methods, e.g., an expandable balloon at the distal end of a catheter shaft. The connecting structures in this embodiment will comprise an elastic material to minimize plastic deformation as the stent is expanded by the balloon catheter. In the preferred configuration, the connecting structures comprise superelastic material, such as a shape memory alloy that recovers to an expanded configuration at temperatures below body temperature (e.g., Nitinol™, Elgiloy™ or the like). The superelastic material generally will not take a permanent set during incatheter deployment, which allows bending of the connecting structures in the vasculature as the stent is delivered to the target site. In addition, the connecting structures will maintain their rigidity in the expanded configuration, i.e., they are more rigid than the stent frames so that the stent frames (and not the connecting structures) will conform to the geometry of the body lumen.

FIGS. 1–4 illustrate a representative intravascular stent structure 10 having a perforate tubular frame 12 which includes a plurality of independent, flexible ring frames 14. Ring frames 14 preferably have a substantially circular cross-sectional shape, and they have sufficient flexibility to deform into a substantially elliptical shape as the stent structure 10 conforms to tortuous body lumen (discussed in detail below, see FIGS. 3A–3C). Each ring frame 14 includes a plurality of V-shaped segments 20 connected to each other at intersection points 21 (FIG. 4A). Segments 20 are preferably constructed from a tubular or planar element that is deformed and suitably etched or laser cut, as described above. Alternatively, segments 20 may be constructed of a single continuous element, such as a wire, that is deformed into the configuration shown in FIG. 4A. The V-shaped segments 20 provide hoop strength, the ability to radially compress the ring frame 14 for deployment to the target site, and outward radial force against the luminal wall (discussed below).

Figure 2A:
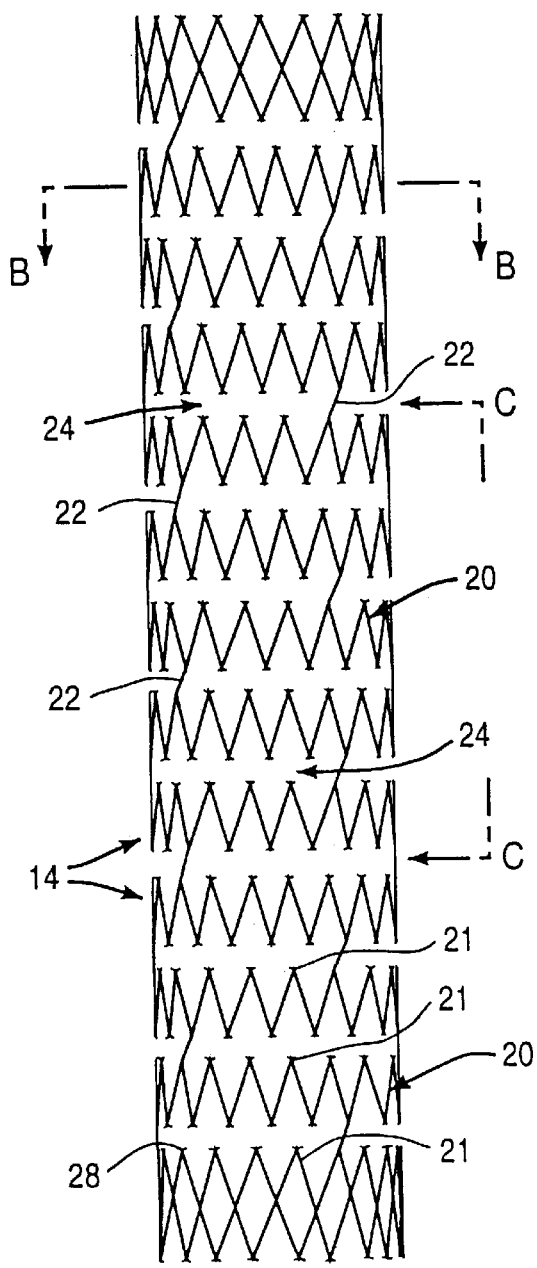
FIG. 2A schematically illustrates one side of the stent-graft of FIG. 1.
Figure 2B:
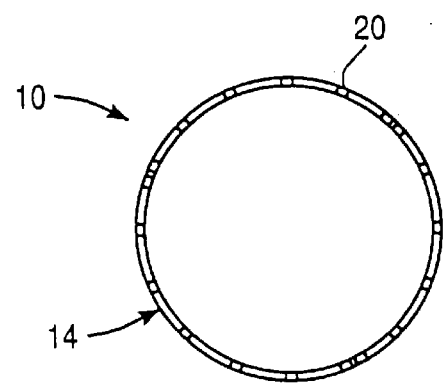
FIG. 2B illustrates a sectional view of the stentraft of FIG. 2A taken along lines B—B.

As shown in FIGS. 1 and 2A, ring frames 14 are preferably connected together with one or more rigid connectors 22 that extend from intersection points 21 between adjoining V-shaped segments 20 to provide a single integral body construction. Connectors 22 comprise a rigid material, such as a metal wire or the like, to maintain a substantially constant distance between adjoining ring frames 14 as the stent structure bends or pivots around curves in the body lumen (see FIGS. 3C and 3D). Connectors 22 allow adjacent ring frames 14 to move axially relative to each other, which provides the entire stent with greater bending flexibility. Usually, connectors 22 will have an axial length of about 10% to 200% of the axial length of ring frames 14. This ratio will usually vary depending on the individual patient, and/or the function of the stent. For example, for treatment of occlusive diseases, it is usually desired to have a greater amount of luminal coverage. Thus, a relatively smaller ratio of connector length to ring frame length will be desired (i.e., around 10% to 50%). On the other hand, for stent-graft applications, less luminal coverage is typically desired, and therefore, a larger ratio of connector length to ring frame length may be employed (i.e., around 100% to 200%).

In an exemplary configuration, connectors 22 will bend when the stent is in the compressed or small diameter configuration (not shown) within the delivery catheter to facilitate the delivery of the stent to the target site within the vasculature. As shown in FIGS. 3C and 3D, once the stent has been radially expanded to a larger diameter configuration, the connectors 22 will be generally rigid enough to minimize or completely prevent bending of connectors 22 (even when the connectors 22 span a curve or bend at the target site in a tortuous body lumen). This is because, in the radially expanded configuration, connectors 22 are positioned further from the longitudinal center line of the stent. Thus, the bending forces are substantially axial (either tensile or compressive) forces at the connectors 22. Connectors 22 are rigid enough to withstand these axial forces to thereby maintain a substantially constant distance between adjacent ring frames 14 as the ring frames 14 bend and deform to conform to the tortuous body lumen.

As shown in FIGS. 1 and 2A, stent structure 10 preferably includes a group of three connectors 22 extending between adjoining frames 14 and spaced uniformly around the circumference of the stent to define three interstitial spaces 24 therebetween. Of course, it will be understood that the present invention may employ more or less than three connectors 22 between adjoining stent frames 14. However, applicant has found that three connectors 22 provides adequate axial stiffness, while allowing the adjoining stent frames 14 to flex in the longitudinal direction to facilitate bending around curves in a body lumen. As discussed below, interstitial spaces 24 also facilitate anchoring the stent 10 to the luminal wall at the target site.

Figure 3A:
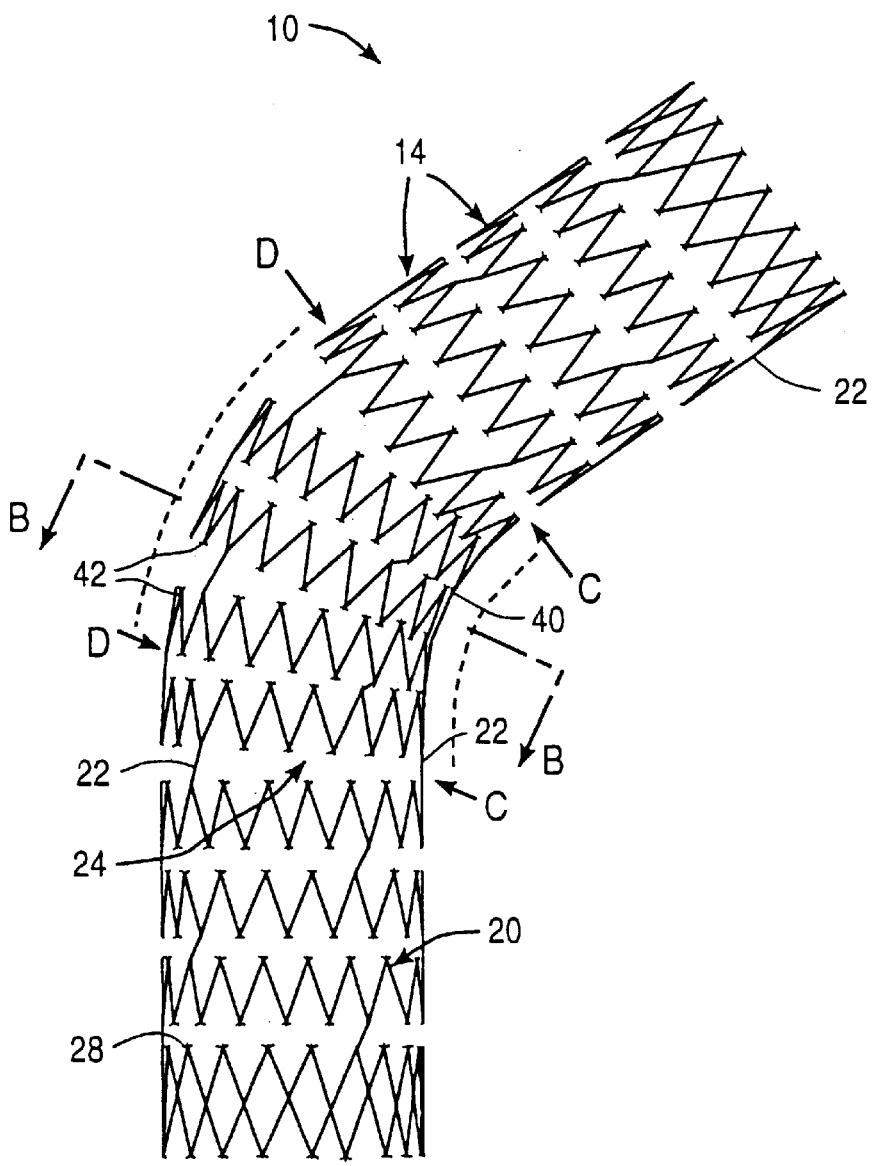
FIG. 3A schematically illustrates one side of the stent-graft of FIG. 1 as the stent conforms to a curve or bend in an anatomical lumen in the expanded configuration.
Figure 3B:
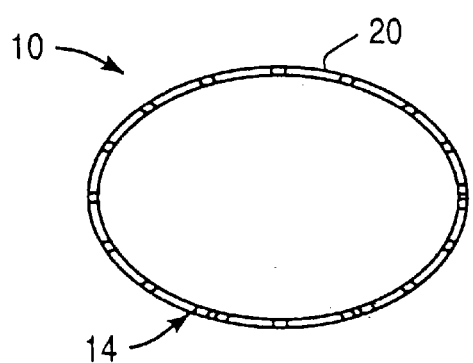
FIG. 3B illustrates a sectional view of the stentgraft of FIG. 3A taken along lines B—B, illustrating the oval cross-sectional shape of one of the deformed ring frames.
Figure 3C:
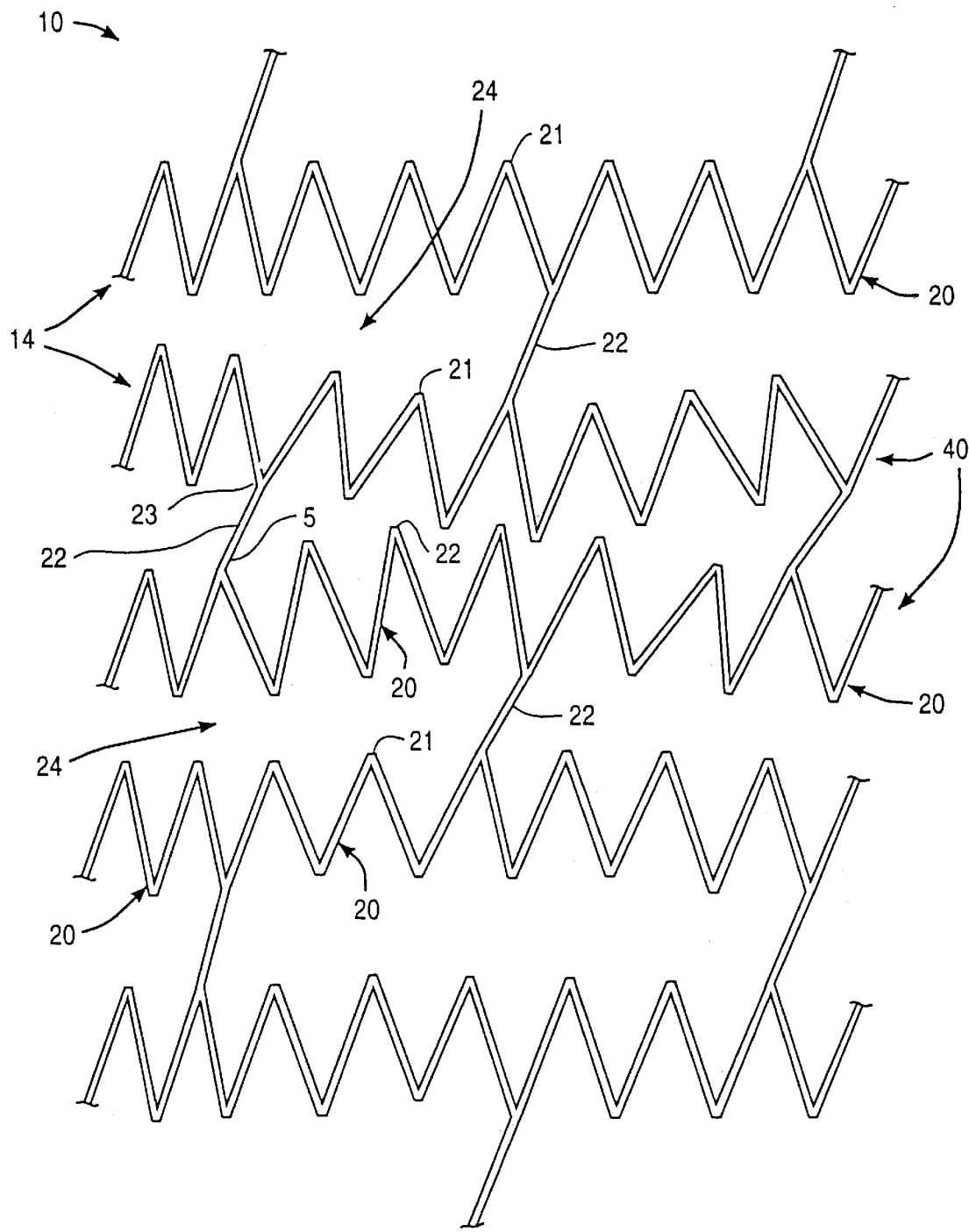
FIG. 3C is an expanded view of a portion of the stent-graft of FIG. 3A taken along lines C—C on the inner side of the curve.
Figure 3D:
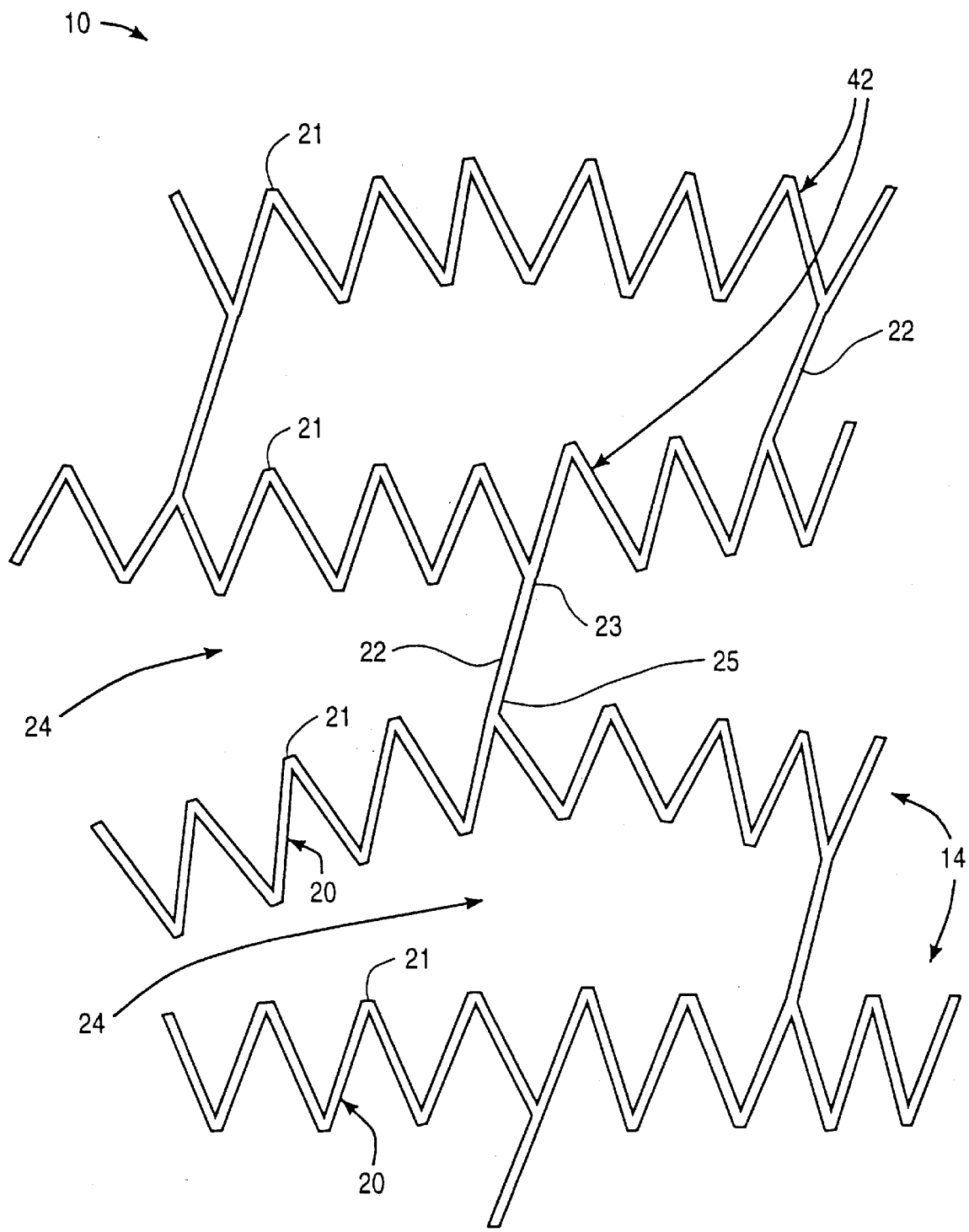
FIG. 3D is an expanded view of a portion of the stent-graft of FIG. 3A taken along lines D—D on the outer side of the curve.

Note that FIG. 3A is merely a schematic representative of the stent in a curved configuration. This figure does not accurately portray the deformation of ring frames 14, as shown more accurately in FIGS. 3B–3D. FIGS. 3C and 3D, in particular, depict the deformation of ring frames 14 when the stent is positioned in a curved portion of a body lumen. As shown in FIG. 3A, the spaces 24 between connectors 22 allow adjoining first portions 40 of ring frames 14 to move towards each other on the inside of a curve and second portions 42 of ring frames 14 to move away from each other on the outside of a curve. This movement causes the ring frames 14 to deform into a partially elliptical shape (FIG. 3B) that conforms to the inner luminal wall at a curved portion of the lumen. In addition, the rigid connectors 22 cause adjacent ring frames 14 to rotate about the longitudinal axis relative to each other as the ring frames 14 conform to the curved portion of the anatomical lumen (FIGS. 3C and 3D).

As shown in FIG. 3C, for example, ring frames 14 move closer together on the inside of the curve. Since connectors 22 maintain substantially the same distance between adjacent ring frames at their end points 23, 25, the ring frames 14 will rotate relative to each other about the longitudinal axis such that the intersection points 21 of the V-shaped segments 20 are no longer parallel to the longitudinal axis (as they are in the straight configuration, see FIG. 2A). Similarly, on the outside of a curve (FIG. 3D), ring frames 14 move away from each other to enlarge interstitial spaces 24. However, connectors 22 maintain a substantially constant distance between their endpoints 23, 25, which causes the ring frames to rotate relative to each other about the longitudinal axis.

Referring again to FIG. 1 connectors 22 of each group are preferably staggered from other connector groups so that adjacent spaces 24 are staggered from each other. Thus, each connector 22 will be aligned with adjacent interstitial spaces 24, which provides more flexibility to the rings frames 14. In addition, this arrangement allows the stent to conform to curves in the body passageway regardless of the orientation of the individual connectors 22 relative to the curve. Thus, the surgeon does not have to map out the body passageway (as is the case with many prior art stents) to determine the optimal orientation for the stent to pass therethrough.

Figure 2C:
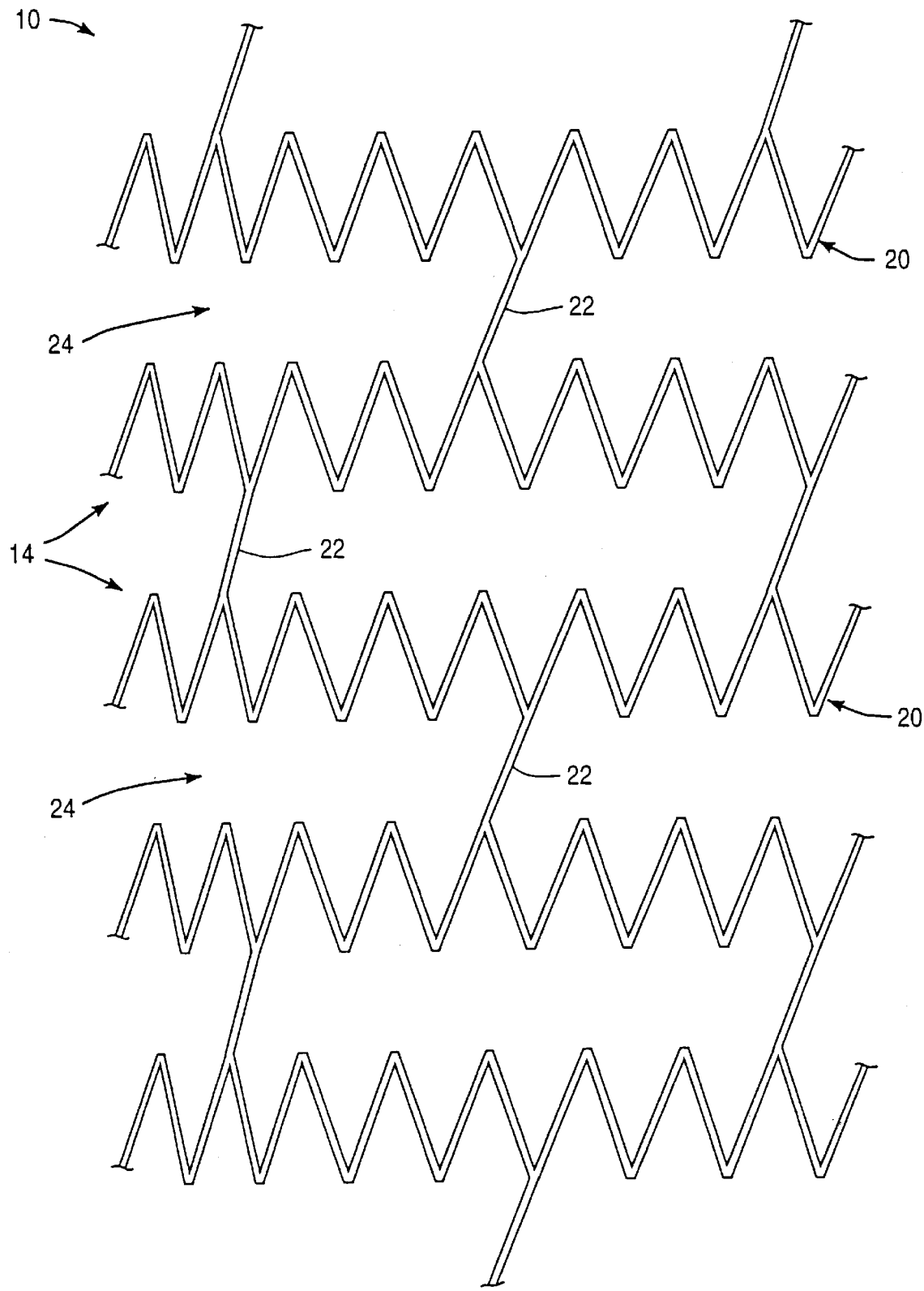
FIG. 2C is an expanded view of one portion of the stent-graft of FIG. 2A taken along lines C—C, illustrating individual ring frames coupled together by rigid connectors.
Figure 4A:
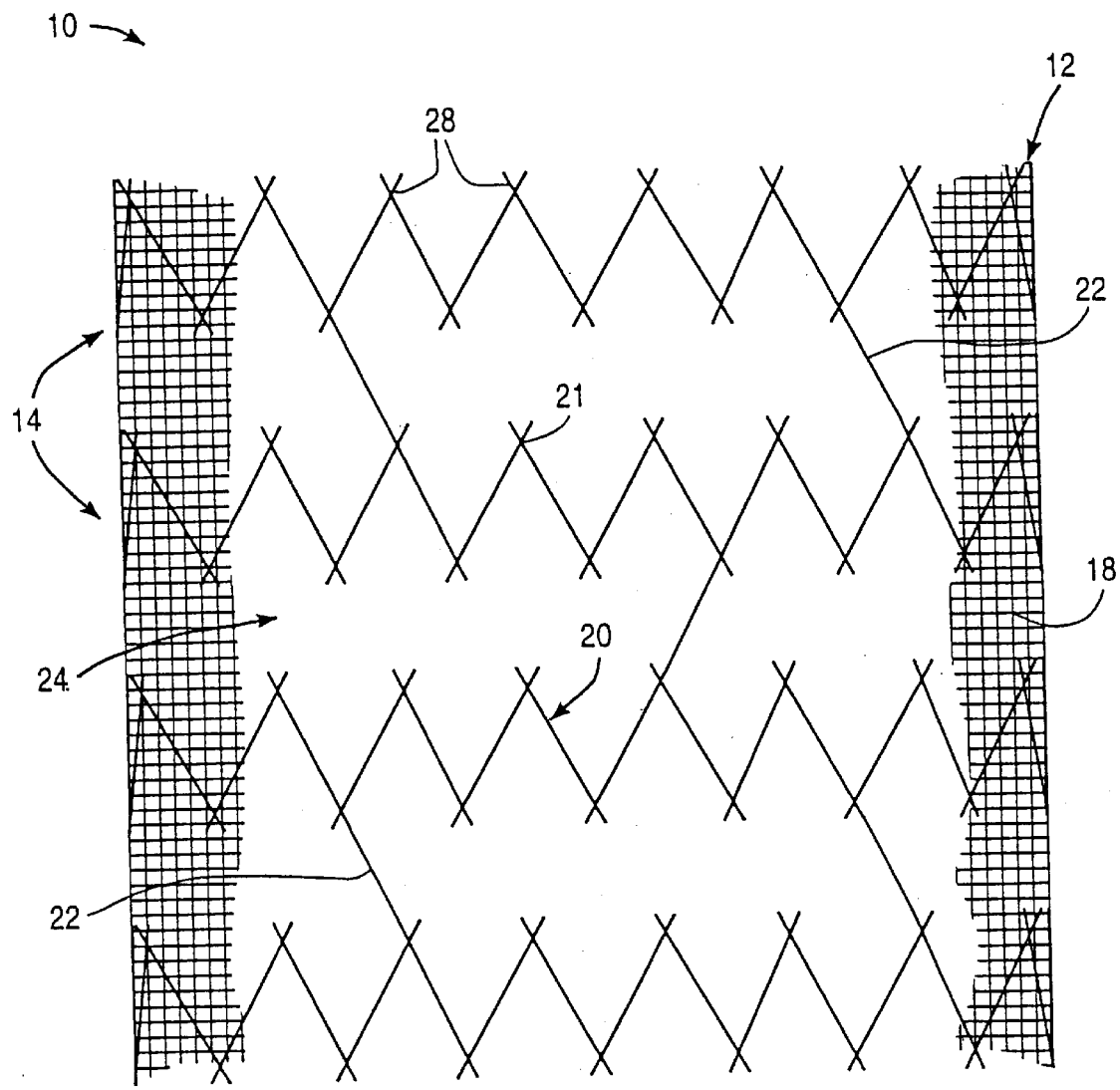
FIG. 4A is an enlarged view of a stent-graft structure illustrating anchor members according to the present invention.

As best shown in FIG. 4A, each ring frame 14 of stent structure 10 includes a plurality of axial extensions or anchor members 28 extending from intersection points 21 of adjoining V-shaped segments 20 (note that anchor members 28 are not shown in FIGS. 1, 2C and 3C). In one embodiment, anchor members 28 comprise relatively sharp points within the interstitial spaces 24 between adjacent ring frames 14. Alternatively, the anchor members may comprise rounded, atraumatic protrusions 27 extending from one or more of the legs of the V-shaped segments 20 to minimize tissue damage (see FIG. 4C). Preferably, a pair of anchor members 28 will extend from each intersection point 21 around ring frames 14. The pair of anchor members 28 are generally parallel to the legs of the V-shaped segments 20 so that the members 28 extend away from each other into interstitial spaces 24. Alternatively, a single anchor member 28' may extend from one of the legs of the V-shaped segments 20 (see FIG. 4B). The single anchor member may extend generally parallel to one of the legs (see member 28) or it may extend generally parallel to the longitudinal axis of the stent (see member 80), or in other directions so long as the anchor member lies substantially in the same plane as the ring frames 14. As shown, the V-shaped segments 20 of adjacent ring frames 14 are preferably staggered relative to each other to minimize contact between the axially extending anchor members 28 extending from opposing V-shaped segments 20. Of course, it will be noted that the invention is not limited to this configuration for anchor members 28. For example, the number and spacing of members 28 may be adjusted depending on the distance between adjacent ring frames 14, the loads exerted on the stent during and after deployment, and other factors.

Figure 4B:
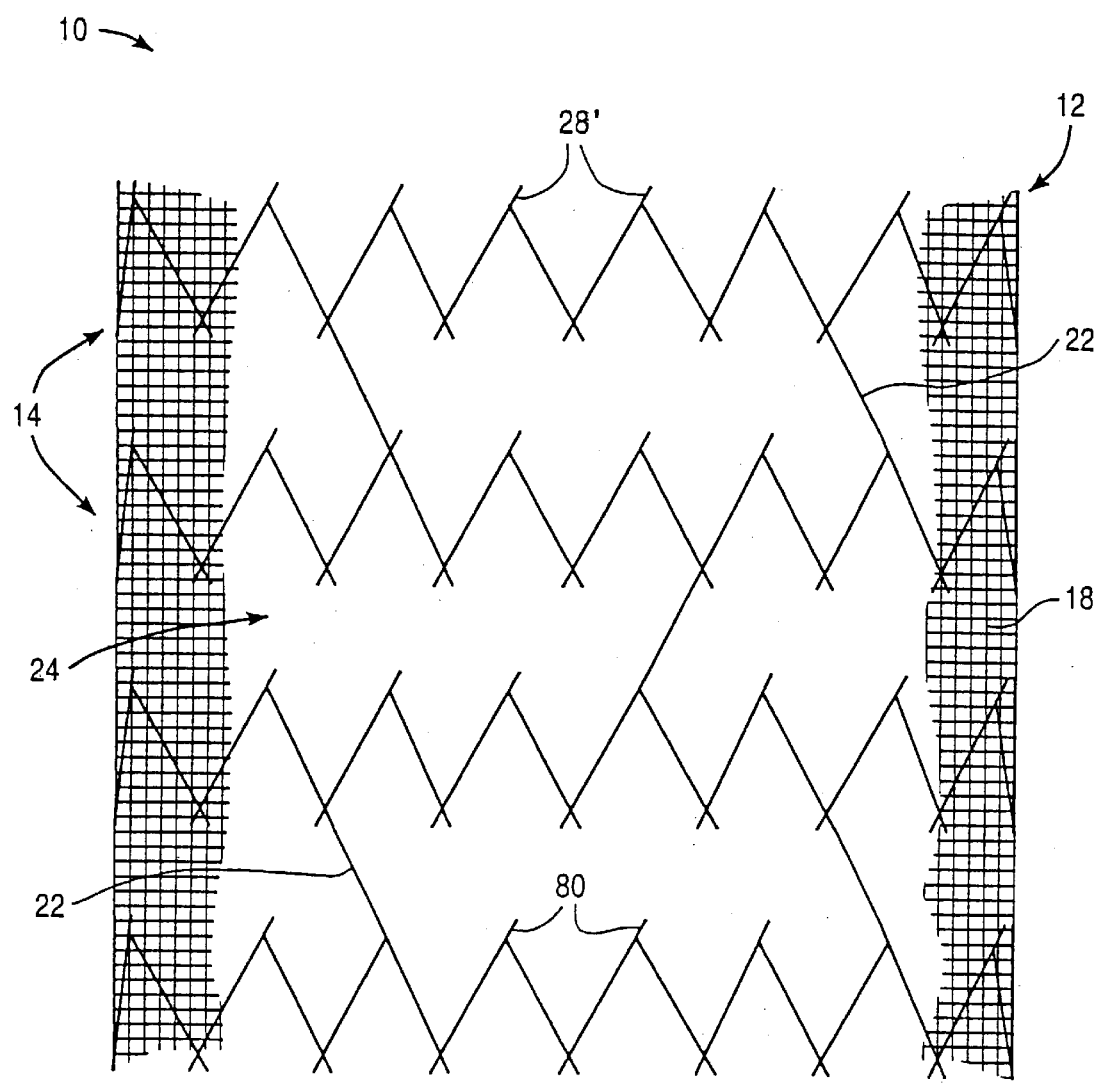
FIGS. 4B and 4C illustrate alternative anchor members for the stent-graft of FIG. 4A.
Figure 4C:
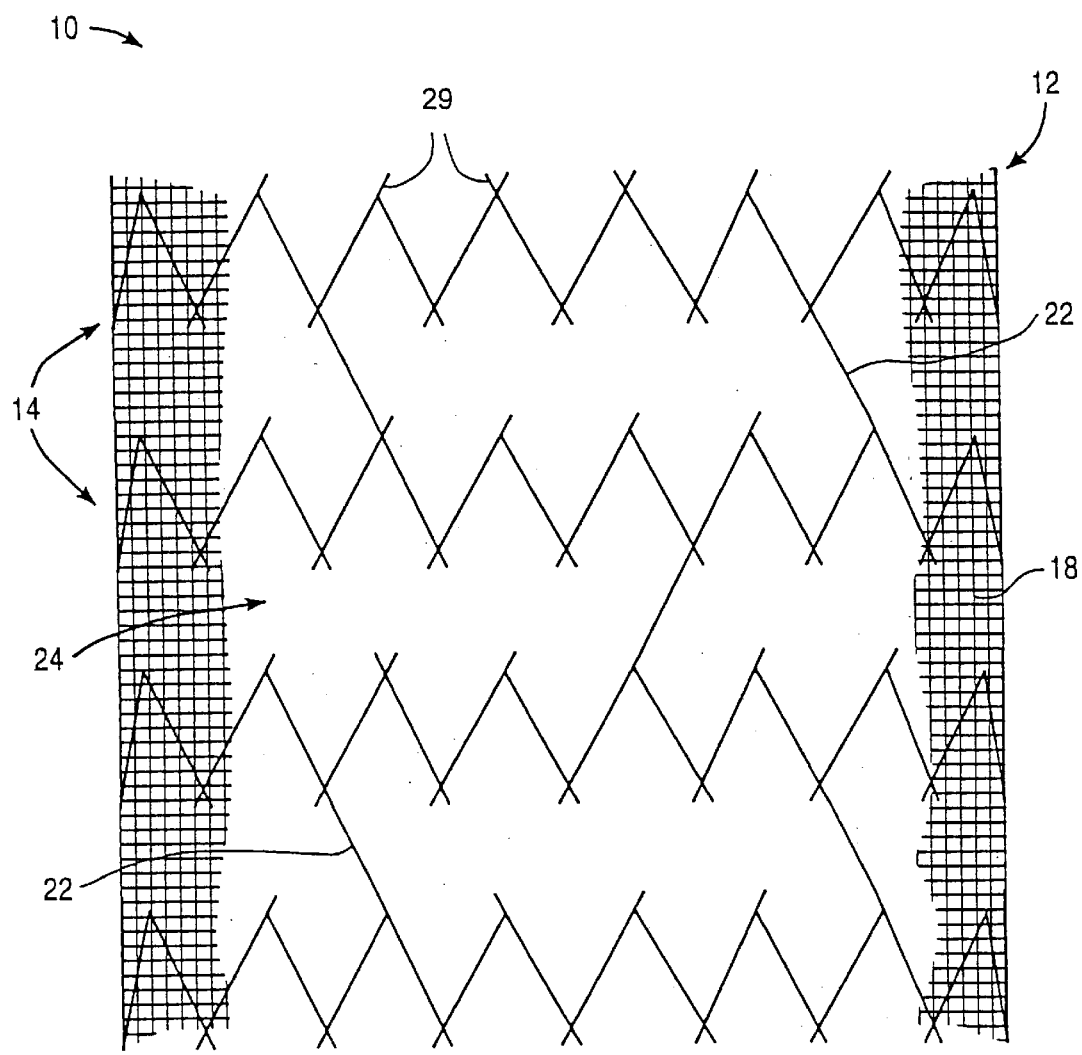

In an exemplary embodiment, the tubular frame 12 supports an inner liner 18 (see FIGS. 4A–4C). Optionally, an outer liner (not shown) is disposed over the ring frames 14, either instead of inner liner 18, or in combination therewith. Inner liner 18 is usually formed from a polymeric sheet material and is typically sutured to frames 14. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other. In a typical embodiment, stent-graft structure 10 is preferably constructed of a thin-walled tubing having a wall thickness in the range of 0.125 millimeters to 0.15 millimeters and having a relatively small collapsed diameter in the range of 1.5 millimeters to 5 millimeters to fit within small tortuous anatomical lumens within the body.

Figures 8A, 8B:
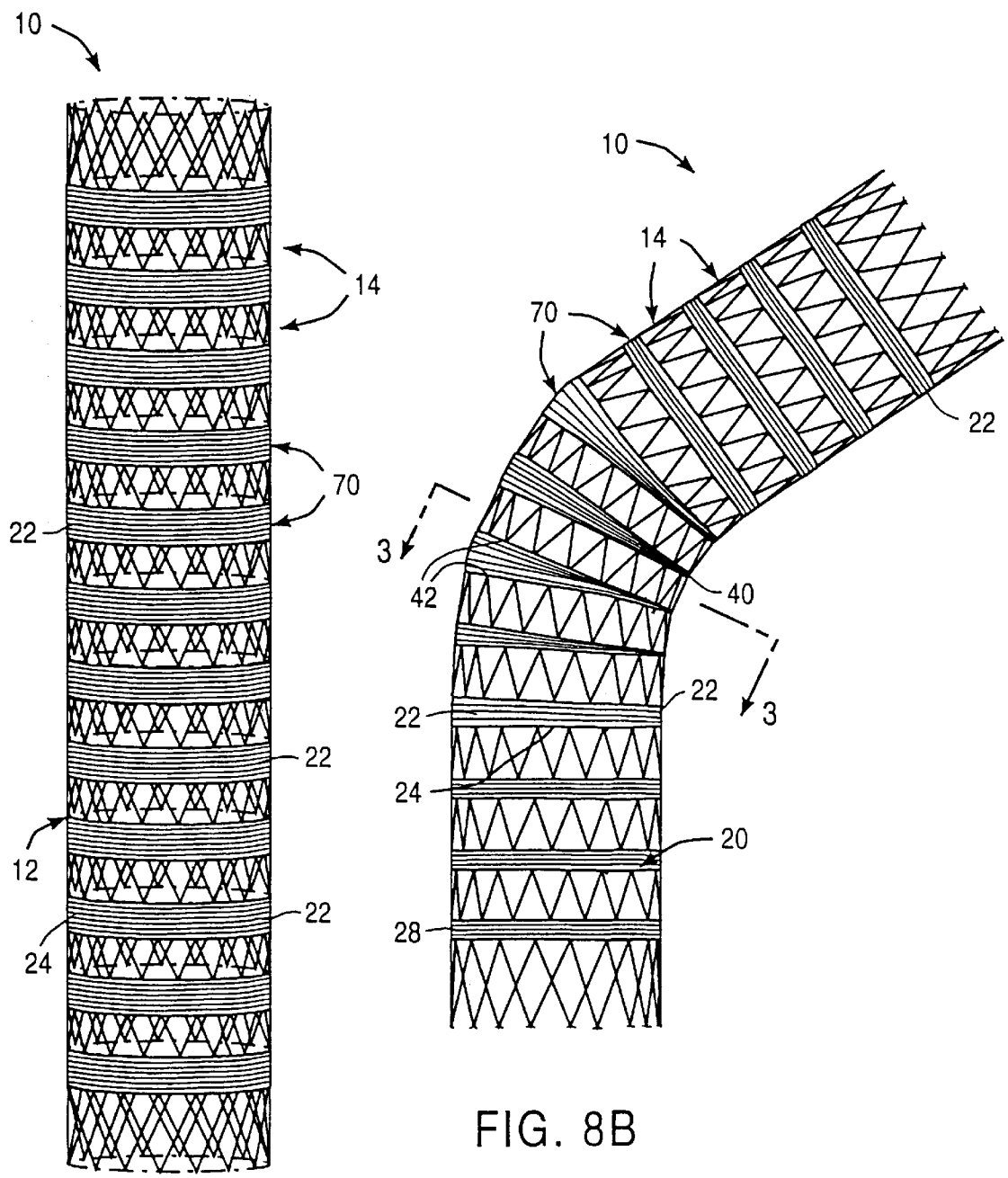
FIG. 8A illustrates an exemplary stent-graft incorporating a selective outer liner covering the spaces between adjacent stent frames.
FIG. 8B schematically illustrates one side of the stent-graft of FIG. 8B as the stent-graft conforms to a curve or bend in an anatomical lumen.

In another embodiment, one or more inner and/or outer liner(s) may be coupled to selected portions of the tubular frame 12. As shown in FIGS. 8A and 8B, for example, a plurality of annular graft liners 70 are coupled to exterior or the interior surfaces of connecting structures 22 (not shown in FIGS. 8A and 8B) to cover interstitial spaces 24 between ring frames 14. Liners 70 may be coupled to structures 22 in any suitable manner, such as heat welding, suturing, adhesive bonding and the like. These liners 70 provide a physical barrier to cell proliferation through spaces 24, while substantially maintaining the flexibility of the stent frames 14. The liners 70 preferably comprise a stretchable material, such as PTFE™, silicone, urethane, corrugated DACRON™, corrugated PTFE™ or the like. This stent-graft of the present invention may be particularly useful for lining or replacing weakened blood vessels, such as in aortic aneurysm repair procedures, e.g., aneurysms occurring in the abdominal aorta, usually beginning below the renal arteries and often extending distally into one or both of the iliac arteries.

Figure 5A:
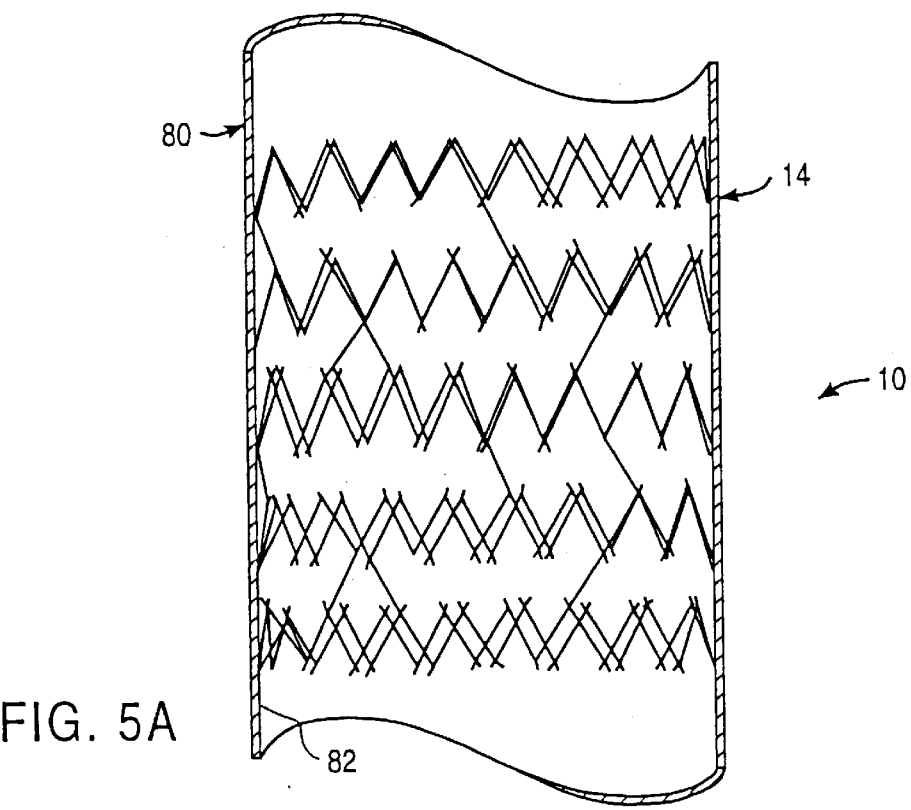
FIGS. 5A and 5B illustrate a method of deploying the stent of FIG. 1 within an anatomical lumen.
Figure 5B:
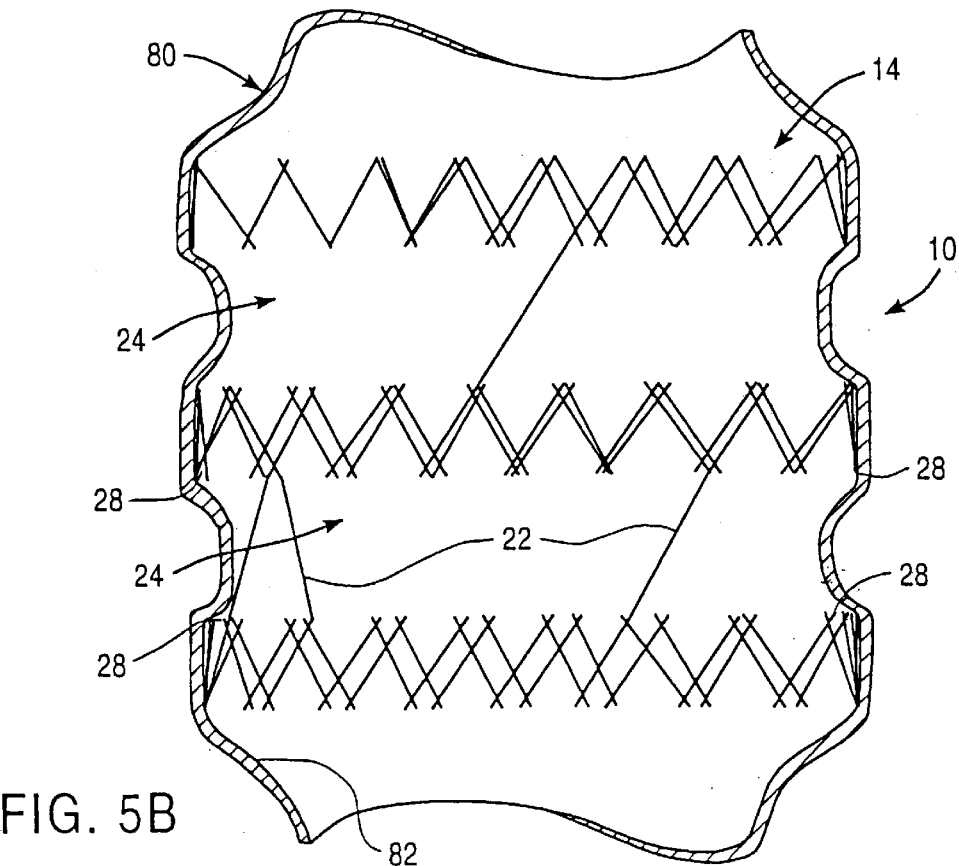

FIGS. 5A and 5B illustrate a method of deploying stent structure 10 according to the present invention. The stent-graft 10 will usually be compressed into a narrow-diameter configuration to facilitate introduction into a body lumen, typically during surgical cutdown or percutaneous introduction procedures. Stent-graft 10 is then delivered through to the desired location within a body lumen 80 in a conventional manner, i.e., via a delivery catheter (not shown). Fluoroscopy and other conventional techniques may be used to ensure that the delivery catheter and stent 10 are delivered to the desired location. As shown in FIG. 5B, once stent-graft 10 is positioned at the target site within body lumen 80, it is controllably expanded radially outward into engagement with the inner walls 82 of body lumen 80. Stent-graft 10 may be radially expanded with a variety of conventional methods, such as expansible balloon, mechanical expanders, shape memory materials or the like. Preferably, stent-graft 10 comprises a self-expanding shape memory material, such as Nitinol™, that expands to an enlarged configuration upon release from the delivery catheter. The shape memory material will generally expand through stress or temperature induced martensite (i.e., upon reaching a critical or $A_f$ temperature). A more complete description of an exemplary method for deploying stent-graft 10 can be found in U.S. Provisional Patent Application Serial No. 60/020,963, filed Jun. 25, 1996 (Attorney Docket No. 16380-55), the complete disclosure of which has previously been incorporated herein by reference.

As shown in FIG. 5B, as stent structure 10 is radially expanded outward, ring frames 14 exert outward pressure on a portion of inner walls 82 of body lumen 82, which forces the soft tissue of the luminal wall 82 to fill a portion of interstitial spaces 24 between adjacent ring frames 14. This design effectively uses portions of the luminal wall as an interlocking mechanical wall with the stent frames to form a substantially continuous wall between stent structure 10 and luminal wall 82. In addition, if pressure from loads, such as blood, vessel contraction and expansion, etc, being to move the stent relative to the luminal wall 82, anchor members 28 will dig into the portions of the inner walls 82 within spaces 24. This secures the stent to the wall by increasing the friction between stent 10 and luminal wall 82, rather than increasing the radial force applied by the stent, which minimizes injury to the vessel wall 82 that may be caused by large radial forces, such as aneurysmal growth, abnormal vessel distension and the like.

Figure 6:
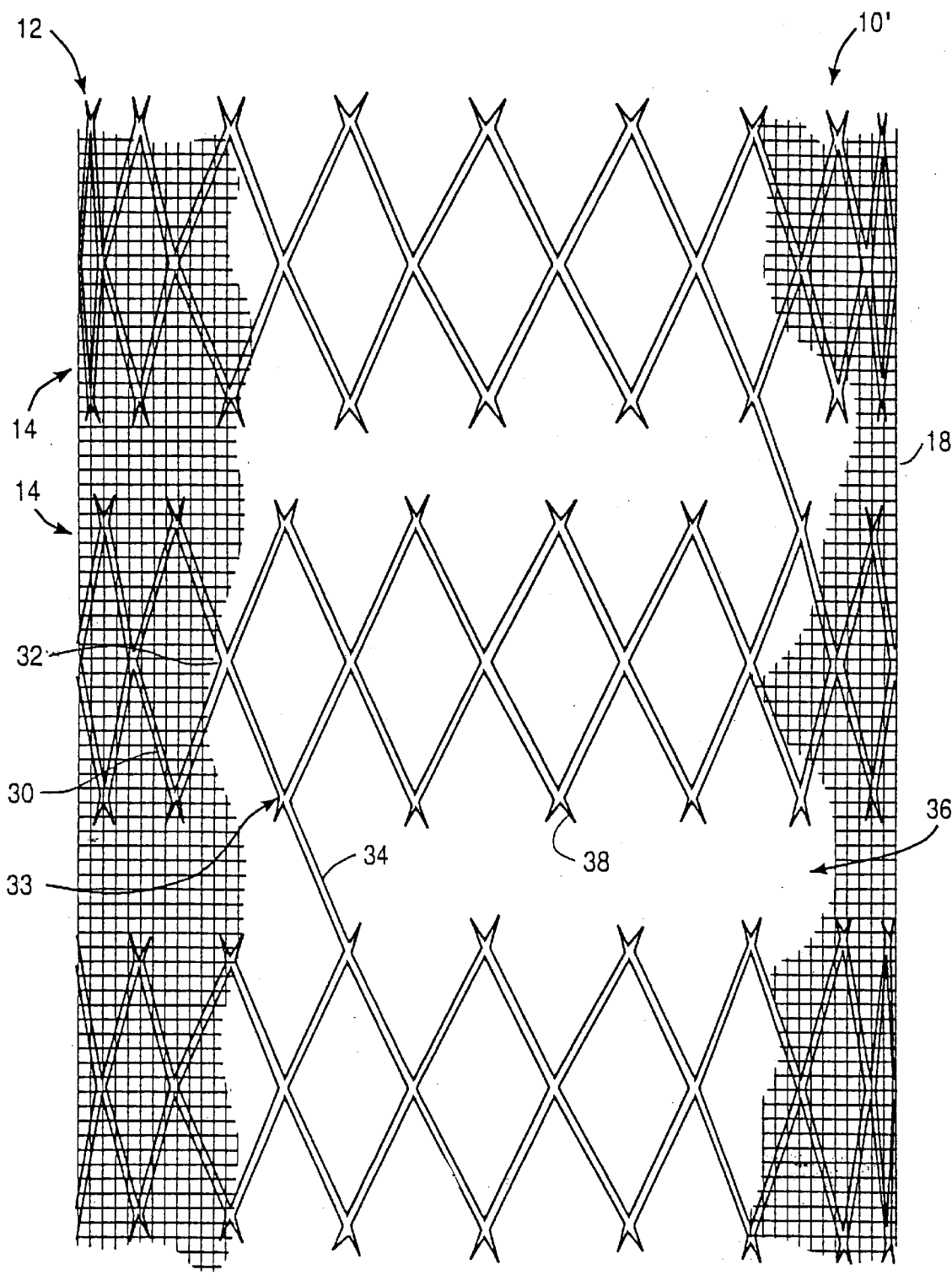
FIG. 6 illustrates another exemplary stent-graft incorporating a plurality of diamond-shaped stent frames according to the present invention.

FIG. 6 illustrates an alternative stent-graft structure 10' according to the present invention. Similar to the stent-graft depicted in FIG. 1, stent-graft structure 10' also includes a perforate tubular frame 12 that includes a plurality of flexible ring frames 14. Note that although FIG. 4 is shown without an inner liner 18, this stent may also include an inner liner, if desired. Each ring frame 14 comprises a plurality of diamond-shaped stent segments 30 that define a pair of laterally or circumferentially facing points 32 and a pair of axial facing points 33. Diamond-shaped stent segments 30 are coupled together at the lateral facing points 32 to form each ring frame 14. As shown, ring frames 14 are also coupled together with three rigid connectors 34, which allow rings frames 14 to move axially relative to each other, providing flexibility to the stent structure. Also similar to the FIG. 1 embodiment, each diamond-shaped segment 30 includes axial protrusions or anchor members 38 extending into interstitial spaces 36 to anchor the stent-graft 10' to the luminal wall, thereby inhibiting migration and/or failure of the stent. Diamond-shaped segments 30 are preferably staggered relative to each other to minimize contact between opposing axial protrusions 38, as shown in FIG. 5.

Figure 7A:
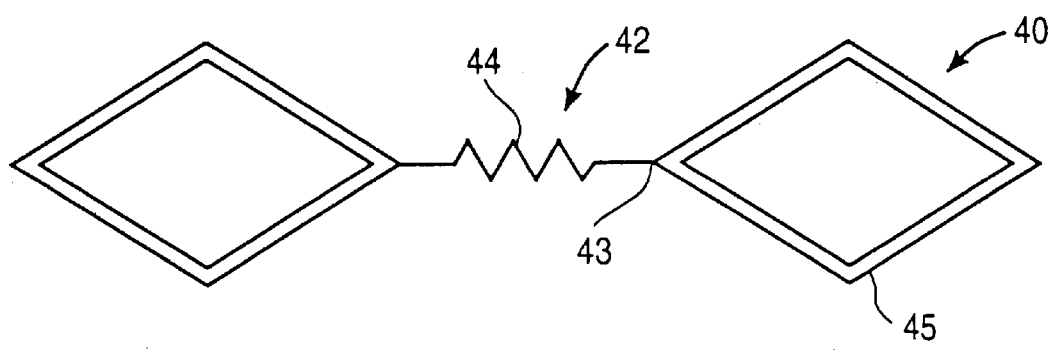
FIG. 7A schematically illustrates a stent according to the present invention incorporating a plurality of diamond shaped stent frames coupled together with springs.
Figure 7B:
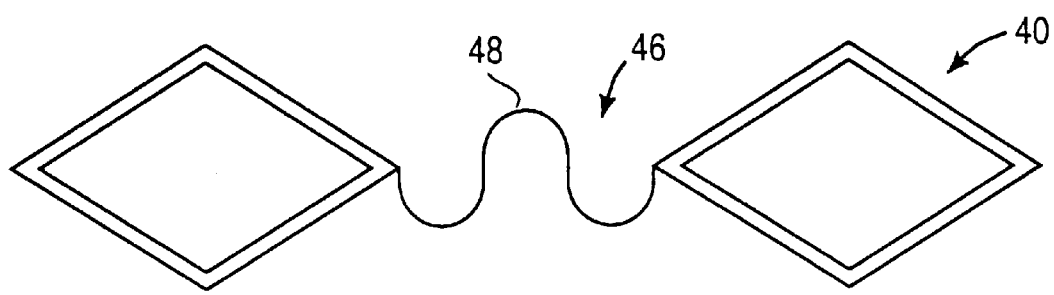
FIGS. 7B–7F schematically illustrate alternative springs for connecting adjoining stent frames according to the present invention.
Figure 7C:
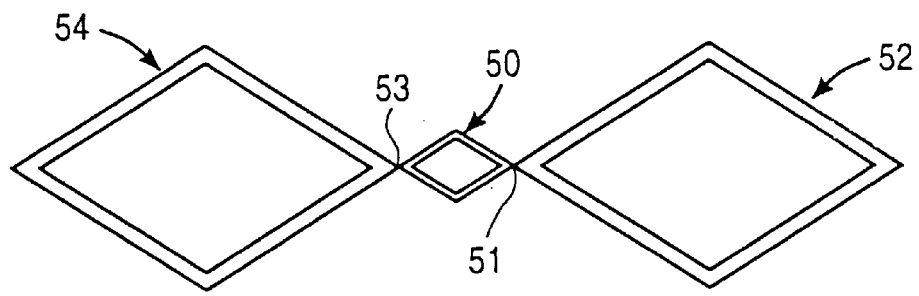
Figure 7D:
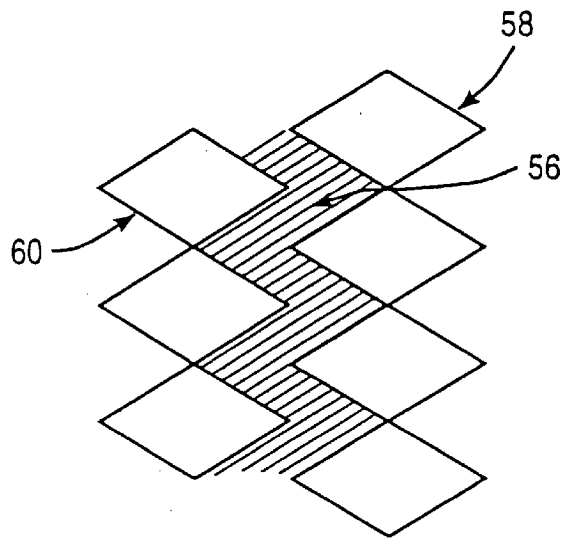
Figure 7E:
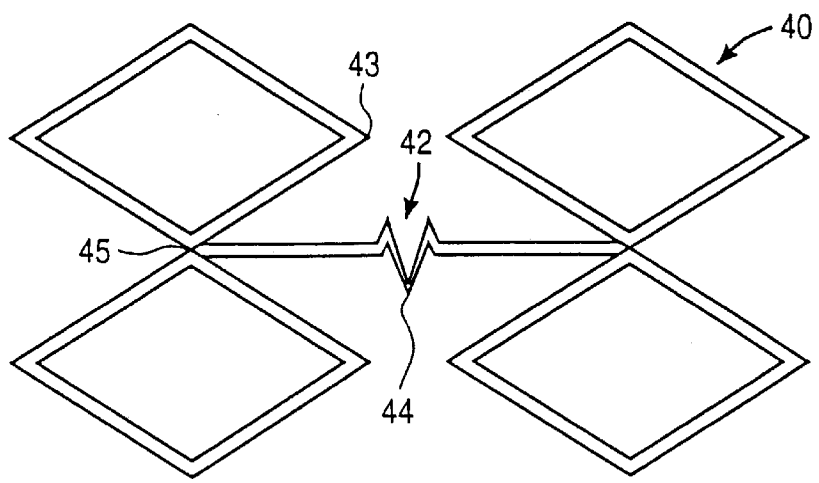

Referring to FIGS. 7A–7F, an alternative embodiment of stent-graft 10 incorporating flexible connectors having a spring force will now be described. Although the connectors of these embodiments will usually be more flexible than the rigid links described above, they will preferably be less flexible than the tubular stent frames 14. In this manner, the connectors will force the stent frames 14 to conform to tortuous body lumens. FIG. 7A illustrates one embodiment wherein a pair of diamond-shaped segments 40 are connected together by an accordion style spring 42 that defines one or more relatively sharp peaks 44. Spring 42 may be connected at laterally facing points 43 of the diamond segments 40 (FIG. 7A), or at axial facing points 45 between adjacent diamond segments 40 (FIG. 7E). Spring 42 may comprise a variety of materials including shape memory materials, such as such as Nitinol™ or Elgiloy™, malleable metals (such as stainless steel), spring steels, polymers (teflon) or elastomers (silicones, latex, rubber), or the like. The spring constant of spring 42 may be adjusted by adjusting the number of peaks 44 in the accordion. Preferably, the spring constant will be sufficient to maintain column stiffness along the axis of the stent structure 10 as well as bending stiffness to allow the entire structure to flex in, for example, a curved blood vessel. Thus, the spring 42 will have a minimum column stiffness to prevent axial compression which leads to wrinkling of the liner(s) (not shown), and a maximum spring constant to allow the stent or stent-graft to bend the required amount.

Figure 7F:
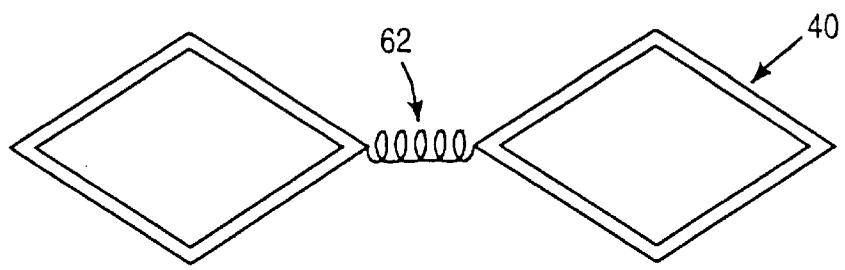

FIGS. 7B through 7F illustrate alternative springs according to the present invention. FIG. 7B illustrates an accordion style spring 46 defining one or more curved peaks 48, rather than sharp peaks 44 as shown in FIG. 7A. The radius of curvature of the peaks 48 may be adjusted to customize the spring constant. FIG. 7C illustrates a small diamond-shaped spring 50 coupled to the laterally facing points 51, 53 of adjoining diamond-shaped stent segments 52, 54. FIG. 7D illustrates an elastomeric material 56 that can be inserted between staggered diamond stent segments 58, 60 to provide a spring therebetween. Finally, FIG. 7F illustrates a coiled spring 62, wherein the pitch, number of coils, diameter and material can be adjusted to adjust the spring constant.

Figure 9:
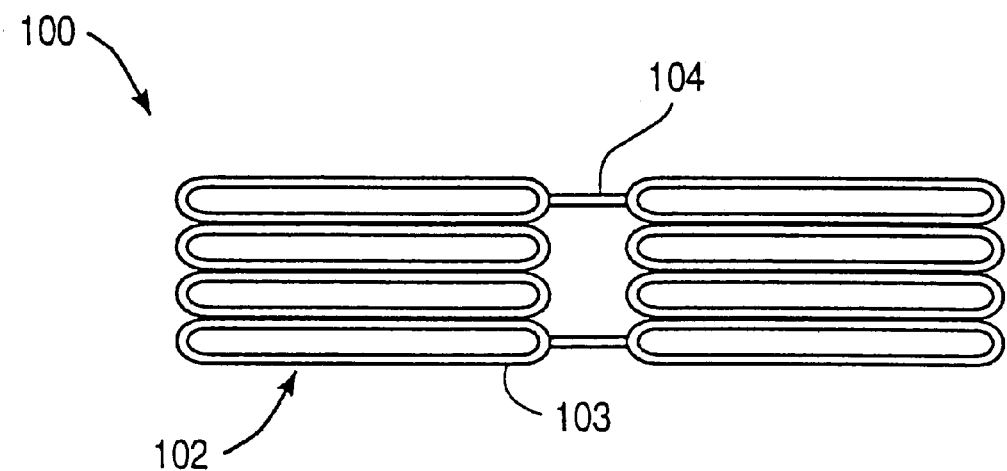
FIG. 9 is an enlarged view of another stent according to the present invention, incorporating malleable stent frames and superelastic connectors.
Figure 10:
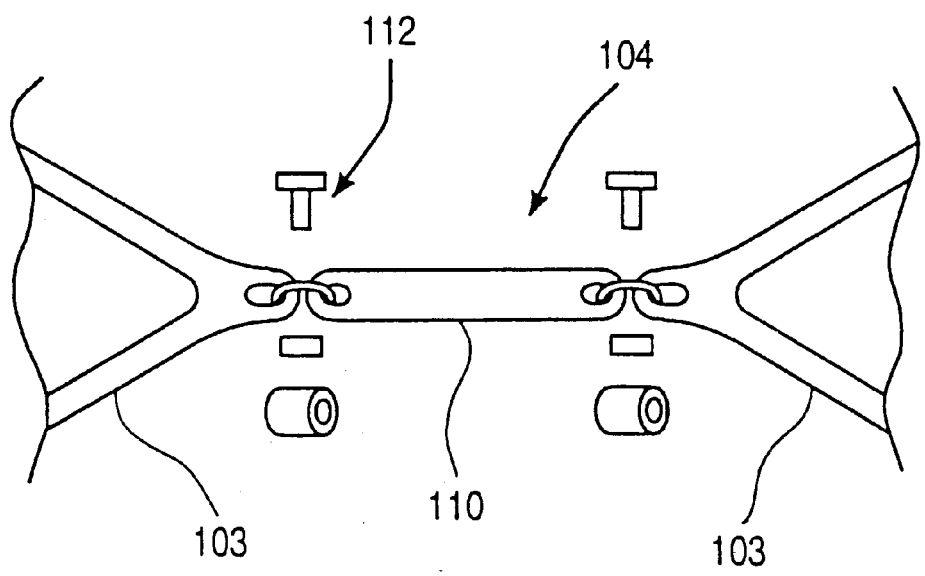
FIG. 10 is an enlarged view of one of the superelastic connectors of FIG. 9.

FIGS. 9 and 10 schematically illustrate a portion of a stent 100 in another embodiment of the present invention. In this embodiment, stent 100 includes a plurality of tubular stent frames 102 comprising a malleable, balloon expandable material, such as stainless steel. The stent frames 102 each include a plurality of malleable rings 103 connected to each other to form the stent frame 102. Some of the rings 103 are connected to rings 103 in adjoining stent frames 102 by rigid connectors 104 that preferably comprise a superelastic material, such as Nitino™, Elgiloy™ or the like. As shown in FIG. 10, connectors 104 are preferably formed as separate links 110 that are attached to adjoining stent frames 102 to connect the stent frames 102 to each other. Connectors may be bonded to stent frames 102 in a variety of ways, such as pins 112, wire wraps, sutures, welds, adhesives, etc. The superelastic connectors 104 will bend during in-catheter (not shown) deployment around curves in body passageways and the superelastic material generally will not take a permanent set during deployment. During balloon expansion, superelastic connectors 104 will experience little to no plastic deformation because the connectors 104 are not significantly involved in the radial expansion of the device. In addition, superelastic connectors 104 generally maintain their rigidity in the expanded configuration (FIG. 9). Thus, connectors 104 will be sufficiently rigid to force stent frames 102 to conform to the tortuous lumen after stent 100 has been deployed at the target site.

Modification and variation can be made to the disclosed embodiments without departing from the subject of the invention as defined by the following claims. For example, although particular stent-graft structure are described above and shown in the figures, the present invention is not intended to be limited to this structure. That is, a variety of grafts, stents or stent-graft designs that are commonly used in this art can be modified according to the present invention to incorporate either the anchor members or the flexible ring frames and rigid connecting links described above. For example, representative conventional stent structures made from metallic tubular materials that are currently marketed as implants for coronary, peripheral, biliary and other vessels include the Palmaz-Schatz™ balloon expandable stent, manufactured by Johnson and Johnson Interventional Systems, Co. and the Memotherm™ stent manufactured by Angiomed, a division of C. R. Bard, Inc. Other stent or graft designs that can be incorporated into the present invention include a coiled structure, such as that described in U.S. Pat. No. 5,476,505 to Limon, an open mesh or weave stent structure formed of helically wound and/or braided strands or filaments of a resilient material, described in U.S. Pat. No. 5,201,757 to Heyn, a filament knitted into a mesh cylinder, described in U.S. Pat. No. 5,234,457 to Andersen, a tubular structure having diamond shaped openings, described in U.S. Pat. Nos. 5,242,399 to Lau or U.S. Pat. No. 5,382,261 to Palmaz, Z-shaped stents as described in U.S. Pat. No. 5,282,824 to Gianturco, continuous wire stents, such as the one described in U.S. Pat. No. 5,292,331 to Boneau, stents formed of filaments that are wound into spiral or other suitable shapes as described in U.S. Pat. No. 5,314,471 to Fountaine, a continuous helix of zig-zag wire and loops described in U.S. Pat. No. 5,405,377 to Cragg and a variety of other types of stents.

What is claimed is:

1. A method for deploying a luminal prosthesis at a target site within an anatomical lumen comprising:

providing at least two flexible tubular stent frames in a compressed configuration, the stent frames being connected with one or more bent, substantially rigid connecting structures;

introducing the tubular stent frames into an anatomical lumen; and deploying the stent frames to conform to a curved portion in the anatomical lumen, wherein the substantially rigid connecting structures are substantially unbent during deployment.

2. The method of claim 1 further comprising implanting the tubular stent frames at a target site within a tortuous anatomical lumen, the stent frames deforming to conform to a geometry of said tortuous anatomical lumen.

3. The method of claim 2 where the stent frames each comprise a radially expansible, malleable material and the rigd connecting structures each comprise a superelastic material, the implanting step comprises:

expanding a radially expansible member within a hollow lumen of the stent frames to radially expand the stent frames at the target site; and allowing the superelastic rigid connecting structures to return to an expanded configuration at the target site.

4. The method of claim 2, wherein the implanting step comprises:

compressing the stent frames and the rigid connecting structures into a radially compressed configuration; and allowing the stent frames and rigid connecting structures to recover to an expanded configuration at the target site.

5. The method of claim 4 wherein the allowing step is carried out by the application of heat from the patient's body.

6. The method of claim 1 wherein a distance between adjoining stent frames at the rigid connecting structure remains substantially constant as the stent frames articulate to conform to the curved portion of the anatomical lumen.

7. The method of claim 1 wherein the prosthesis comprises groups of three rigid connecting structures extending between adjoining stent frames and uniformly spaced around the circumference of the stent frames.

8. The method of claim 1 further comprising deforming the stent frames from a substantially circular cross-section to an elliptical cross-section as the stent frames articulate to conform to the curved portion of the anatomical lumen.

9. The method of claim 1 further comprising lining interstitial spaces between the stent frames with one or more graft liners to inhibit cell proliferation therebetween.

10. The method of claim 1 further comprising:
   positioning the stent frames at the target site within the anatomical lumen;
   radially expanding the tubular stent frames; and
   engaging the luminal wall with one or more anchor members of the stent frames to secure the prosthesis to the luminal wall.

11. The method of claim 10 wherein the radially expanding step includes forcing portions of the luminal wall into interstitial spaces between adjoining stent frames and axially penetrating said luminal wall portions with the anchor members to form a substantially continuous mechanical wall with said luminal wall portions and said stent frames.

12. The method of claim 10 wherein each stent frame comprises a plurality of V-shaped elements defining intersection points between adjoining V-shaped elements, and the anchor members comprise one or more protrusions extending axially outward from the intersection points of a group of the V-shaped elements.

13. The method of claim 10 wherein each stent frame comprises a plurality of diamond-shaped elements defining laterally facing points and axially facing points, the diamond-shaped elements connecting to each other at the laterally facing points and the anchor members comprising protrusions extending axially outward from the axially facing points of a group of the diamond-shaped elements.

14. A method for deploying a luminal prosthesis at a target site within
   a tortuous anatomical lumen comprising:
      positioning a compressed luminal prosthesis having at least two flexible tubular stent frames connected together at points by one or more substantially rigid connecting structures at the target site within the anatomical lumen wherein said substantially rigid connecting structures are configured to bend when compressed; and
      deforming the stent frames a sufficient amount such that the stent frames substantially conform to an inner wall surface of the anatomical lumen, and wherein said substantially rigid connecting structures maintain the stent frames at a constant distance at the connection points.

15. A method for deploying a radially expansible luminal prosthesis comprising:
   providing at least two tubular stent frames sized for delivery through an anatomical lumen, each stent frame having a longitudinal axis, an open proximal end, and an open distal end;
   introducing the tubular stent frames in an anatomical lumen; and
   deforming a plurality of substantially rigid connecting structures configured in groups extending between and movably connecting adjoining stent frames to allow flexing of the prosthesis along the longitudinal axis wherein the substantially rigid connecting structures are more rigid than the tubular stent frames.

16. The method of claim 15, wherein the connecting structures within each group are uniformly spaced around a circumference of the stent frames and staggered relative to each other along the longitudinal axis of the prosthesis such that each connecting structure is centered between two of the connecting structures in an adjacent group.

17. The method of claim 15, wherein the stent frames have sufficient flexibility to deform into a configuration substantially conforming to a curved portion of an anatomical lumen.

18. The method of claim 15, wherein the connecting structures are substantially more rigid than the stent frames.

19. The method of claim 15, wherein said deforming of the plurality of substantially rigid connecting structures is such that each stent frame defines a transverse cross-sectional shape and wherein the cross-sectional shapes of each stent frame changes as the stent frames conform to a longitudinally curved portion of an anatomical lumen.

20. The method of claim 19, wherein the connecting structures define a distance between adjoining stent frames that remains substantially constant as the cross-sectional shapes of each stent frame changes to conform to a longitudinally curved portion of an anatomical lumen.

21. The method of claim 19, wherein the transverse cross-sectional shape is substantially elliptical.

22. The method of claim 15, wherein the connecting structures each comprise a single rigid wire.

23. The method of claim 15, wherein the groups of connecting structures each comprise two connecting structures extending between adjoining stent frames.

24. The method of claim 15, wherein the groups of connecting structures each comprise three connecting structures extending between adjoining stent frames.

25. The method of claim 15, wherein the groups of connecting structures each comprise four connecting structures extending between adjoining stent frames.

26. The method of claim 15, wherein each stent frame includes a plurality of body segments connected together to form the stent frame and at least one of a plurality of anchor members with tapering ends extending axially from the body segments and substantially parallel to the longitudinal axis of the stent frame for securing the prosthesis to the luminal wall.

27. The method of claim 26, wherein the body segments comprise V-shaped elements defining intersection points between adjoining V-shaped elements, and wherein the at least one of a plurality of anchor members comprise at least one protrusion extending axially outward from the intersection points of a group of the V-shaped elements.

28. A method comprising:
   providing a plurality of tubular stent frames sized for delivery through an anatomical lumen, each stent frame having open proximal and distal ends along a longitudinal axis of the prosthesis; and
   connecting each of said tubular stent frames with a plurality of bendable connecting structures configured in groups extending between adjoining stent frames, the connecting structures being more rigid than the stent frames so that the stent frames deform axially when the prosthesis conforms to a longitudinally curved portion of an anatomical lumen.

29. The method of claim 28, wherein each group defines a plurality of even circumferential interstitial spaces between the connecting structures of the group, and wherein each connecting structure is centered along an interstitial space of an adjacent group.

30. The prosthesis of claim 28, wherein alternating groups are aligned axially.

* * * * *